United States Patent
Ross

(10) Patent No.: US 7,674,421 B2
(45) Date of Patent: Mar. 9, 2010

(54) METHOD OF MAKING A GUIDE CATHETER

(75) Inventor: Christopher Daniel Ross, Davie, FL (US)

(73) Assignee: Engineering Resources Group, Inc., Davie, FL (US)

( * ) Notice: Subject to any disclaimer, the term of this patent is extended or adjusted under 35 U.S.C. 154(b) by 0 days.

(21) Appl. No.: 11/954,066

(22) Filed: Dec. 11, 2007

(65) Prior Publication Data

US 2008/0088055 A1   Apr. 17, 2008

Related U.S. Application Data

(62) Division of application No. 10/955,275, filed on Sep. 30, 2004, now Pat. No. 7,306,585.

(51) Int. Cl.
*B29B 17/00* (2006.01)
*B32B 37/00* (2006.01)
*A61M 25/00* (2006.01)

(52) U.S. Cl. .................. 264/342 R; 156/84; 156/85; 156/86; 264/171.27; 264/171.28; 264/173.14; 264/173.19; 264/210.1; 264/210.2; 264/248; 264/271.1; 264/294; 264/320; 604/523; 604/527

(58) Field of Classification Search ............ 264/171.27; 604/526, 527
See application file for complete search history.

(56) References Cited

U.S. PATENT DOCUMENTS

| | | | |
|---|---|---|---|
| 3,416,531 A | 12/1968 | Edwards | |
| 3,924,632 A | 12/1975 | Cook | |
| 4,323,071 A | 4/1982 | Simpson et al. | |
| 4,516,972 A | 5/1985 | Samson | |
| 4,842,590 A | 6/1989 | Tanabe et al. | |
| 5,019,057 A | 5/1991 | Truckai et al. | |
| 5,201,314 A * | 4/1993 | Bosley et al. | 600/458 |
| 5,403,292 A * | 4/1995 | Ju | 604/527 |
| 5,591,142 A | 1/1997 | Van Erp | |
| 5,755,704 A | 5/1998 | Lunn | |
| 5,782,811 A | 7/1998 | Samson et al. | |
| 5,827,242 A * | 10/1998 | Follmer et al. | 604/526 |
| 5,868,718 A * | 2/1999 | Pepin et al. | 604/264 |
| 5,891,114 A | 4/1999 | Chien et al. | |
| 6,036,682 A * | 3/2000 | Lange et al. | 604/529 |
| 6,077,258 A * | 6/2000 | Lange et al. | 604/527 |
| 6,106,510 A | 8/2000 | Lunn et al. | |
| 6,143,013 A | 11/2000 | Samson et al. | |
| 6,187,130 B1 | 2/2001 | Berard et al. | |
| 6,210,396 B1 | 4/2001 | MacDonald et al. | |

(Continued)

OTHER PUBLICATIONS

Pebax Resins; Polymers Overview; Internet Article; www.atofinachemicals.com, Atofina Chemicals; 2002.

(Continued)

*Primary Examiner*—Jeffrey Wollschlager
(74) *Attorney, Agent, or Firm*—Gordon & Jacobson, PC

(57) ABSTRACT

A guide catheter shaft is formed from an inner tube structure and a multilayer sheath around the inner tube structure. The multilayer sheath includes an intermediate sheath and a shrink tube layer. The intermediate sheath is disposed around the inner tube and realized from a melt-processible first polyether-block amide material. The shrink tube layer is disposed around the intermediate sheath and realized from a different second polyether-block amide (e.g. a cross-linked polyether-block amide material) having a shrink temperature range greater than a melt temperature range of the first polyether-block amide material. The resulting structure is heated at a temperature within the shrink temperature range such that the outer shrink tube layer shrinks and the intermediate layer melts to thereby bond the multilayer sheath to the inner tube.

13 Claims, 4 Drawing Sheets

U.S. PATENT DOCUMENTS

| | | |
|---|---|---|
| 6,245,053 B1 | 6/2001 | Benjamin |
| 6,500,285 B2 * | 12/2002 | Pepin et al. .................... 156/86 |
| 6,503,353 B1 * | 1/2003 | Peterson et al. ............... 156/86 |
| 6,706,018 B2 | 3/2004 | Westlund et al. |
| 2002/0156459 A1 | 10/2002 | Ye et al. |
| 2004/0073158 A1 | 4/2004 | Shah et al. |
| 2005/0228429 A1 | 10/2005 | Burgmeier et al. |

OTHER PUBLICATIONS

Palladium "Pebax" Heat Shrink Tubing; Cobalt Polymers; downloaded from Internet Apr. 26, 2004; www.cobaltpolymers.com.

Medical Tubing Offers More (and Less) to Device Makers; Internet Article: www.devicelink.com; 2002.

Thin Wall Heat Shrink Tubing in Medical Device Mfg.; Advanced Polymers, Inc.; 1999.

Wiseguide Guide Catheter; BostonScientific; 2004.

Guider Softip XF Guide Catheters; Boston Scientific; www.bostonscientific.com; 2004.

* cited by examiner

METHOD OF MAKING A GUIDE CATHETER

CROSS-REFERENCE TO RELATED APPLICATION

This application is a divisional of U.S. application Ser. No. 10/955,275, filed on Sep. 30, 2004, to be issued as U.S. Pat. No. 7,306,585, on Dec. 11, 2007, which is hereby incorporated by reference herein in its entirety.

BACKGROUND OF THE INVENTION

1. Field of the Invention

This invention relates broadly to catheters. More particularly, this invention relates to guide catheters for introducing medical devices and/or therapeutic agents into a body of a patient.

2. State of the Art

Guide catheters are used in surgical applications to provide a passageway through which medical devices and/or therapeutic agents may be introduced within the body of a patient. In intravascular and coronary applications, such medical devices typically include balloon dilation catheters, guide wires or other therapeutic devices and the therapeutic agents typically include contrast media or other therapeutic fluids.

A guide catheter includes a follow shaft defining an inner channel through which the medical devices or agents are delivered once the shaft has been inserted into the body. The inner channel typically comprises a lubricous material such as polytetrafluoroethylene (PTFE), commonly known as TEFLON®, together with a metal braid surround and a flexible durable outer sheath. The outer sheath is typically formed from a polyether-block amide material marketed under the trademark PEBAX® which is commercially available from Atofina Chemicals Inc. of King of Prussia, Pa.

The shaft is typically manufactured by placing fluorinated ethylene-propylene (FEP) shrink tubing over an assembly that includes a mandrel with the PTFE inner channel, the metal braid surround, and the PEBAX® outer sheath. The assembly is heated to activate the FEP shrink tubing and melt the PEBAX® outer sheath. The FEP shrink tubing is then removed and discarded, and the mandrel is removed leaving the elongate shaft. The use of such FEP shrink tubing adds significant material costs to the guide catheter. Moreover, the labor and tooling required to remove the FEP shrink tubing adds significant manufacturing costs to the guide catheter.

Thus, there remains a need in the art to provide a guide catheter with lower material and manufacturing costs. The present invention fulfills these and other needs, and addresses other deficiencies of the prior art implementations and techniques.

SUMMARY OF THE INVENTION

It is therefore an object of the invention to provide a guide catheter that avoids the high material costs of FEP shrink tubing.

It is another object of the invention to provide a guide catheter that avoids the manufacturing costs of the process steps and tooling required to remove FEP shrink tubing.

It is a further object of the invention to provide a guide catheter than is suitable for a wide variety of applications, including intravascular and coronary applications.

It is also an object of the invention to provide a guide catheter that enables positioning, guiding and use in conjunction with fluoroscopic and/or ultrasonic imaging techniques.

In accord with these objects, which will be discussed in detail below, an improved guide catheter includes a hollow elongate shaft defining a channel adapted to pass medical devices and/or therapeutic agents therethrough. The hollow elongate shaft (or hollow elongate shaft section) includes an inner tube and a multilayer sheath formed on the outer surface of the inner tube. The multilayer sheath includes an intermediate layer derived from a first polyether-block amide material (e.g., PEBAX®) and an outer layer derived from a different polyether-block amide (e.g. a cross-linked polyether-block amide material). Reinforcing material (such as a braid of reinforcing filament) may also be part of the multilayer sheath. Preferably, the second polyether-block amide layer of the outer layer provides a shrink tube with a shrink temperature greater than a glass transition temperature for the first polyether-block amide material of the intermediate layer. In this configuration, the shaft is formed by heating the intermediate layer and outer layer at the shrink temperature such that the outer shrink layer shrinks and the intermediate layer melts to thereby bond the multilayer sheath to the inner tube. The outer shrink tube layer remains as part of the elongate shaft. The inner tube is preferably formed from a lubricous polymeric material such as PTFE or the like.

It will be appreciated that the improved guide catheter of the present invention avoids the high material costs of FEP shrink tubing (or other shrink tubing type) as well as the manufacturing costs of the process steps and tooling required to remove FEP shrink tubing (or other shrink tubing type).

According to one embodiment of the invention, the reinforcing material may include a material that is radio-opaque and/or ecogenic to facilitate positioning, guiding and use in conjunction with fluoroscopic and/or ultrasonic imaging techniques.

Additional objects and advantages of the invention will become apparent to those skilled in the art upon reference to the detailed description taken in conjunction with the provided figures.

DETAILED DESCRIPTION OF THE PREFERRED EMBODIMENTS

As used herein, the term "melt-processible" means that the given thermoplastic material is processible into final shapes by methods employing heat, such as extrusion, injection molding, hot compression molding, or other means. The term "melt temperature" and "melt temperature range" refers to a temperature and temperature range, respectively, of the heat that is applied to a melt-processable thermoplastic material in processing the material into its finals shape. Finally, the term "shrink temperature" and "shrink temperature range" refers to a temperature and temperature range, respectively, of the heat that is applied to a shrinkable thermoplastic material in processing the material to activate the material (i.e., make it shrink).

Figure 1:
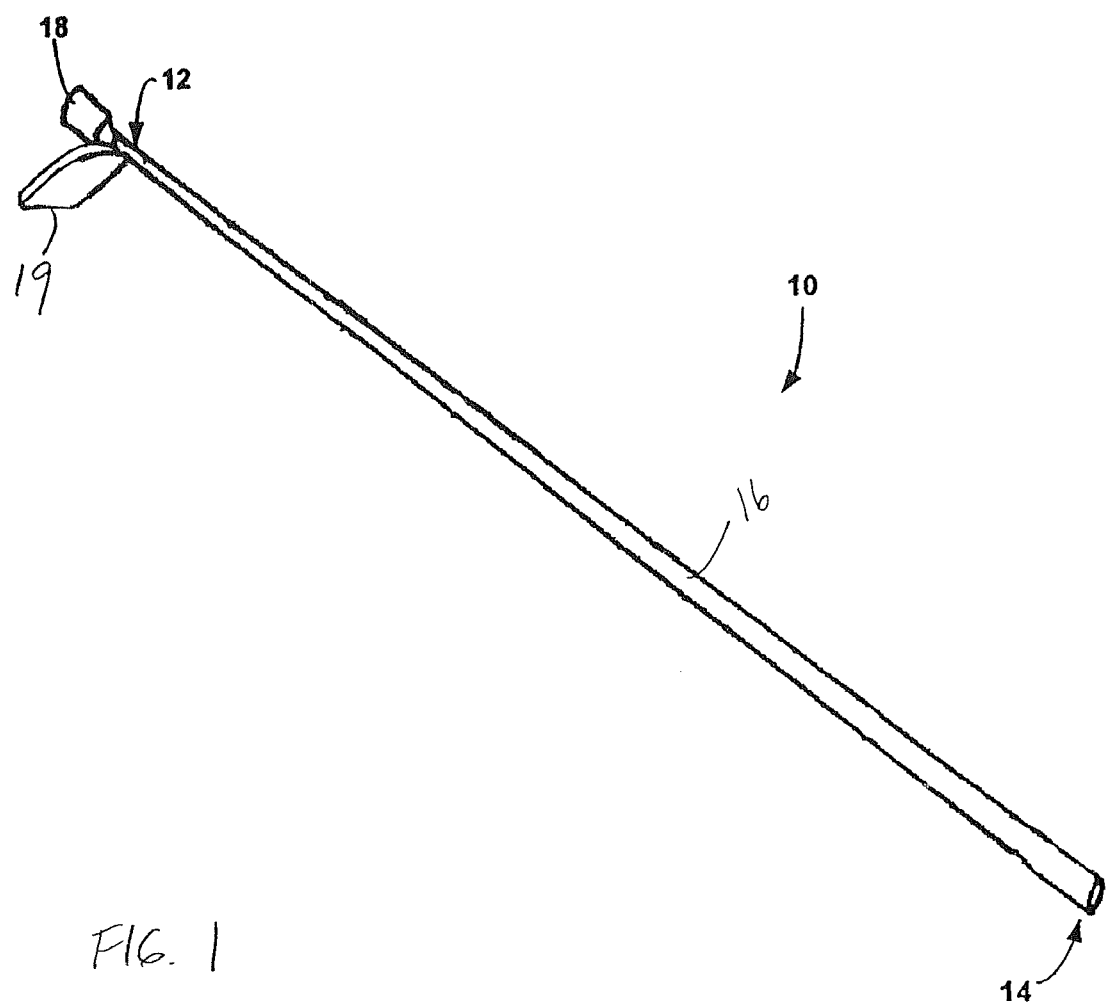
FIG. 1 is a perspective view of a guide catheter.

Turning now to FIG. 1, there is shown a perspective view of a guide catheter 10 including a proximal end 12, distal end 14, and a hollow elongate shaft 16 extending between the proximal end 12 and the distal end 14. The hollow elongate shaft 16 defines a channel 20 (not shown in FIG. 1) through which medical devices and/or therapeutic agents may be introduced within the body of a patient. In intravascular and coronary applications, such medical devices typically include balloon dilation catheters, guide wires or other therapeutic devices and the therapeutic agents typically include contrast media or other therapeutic fluids.

Figure 3:
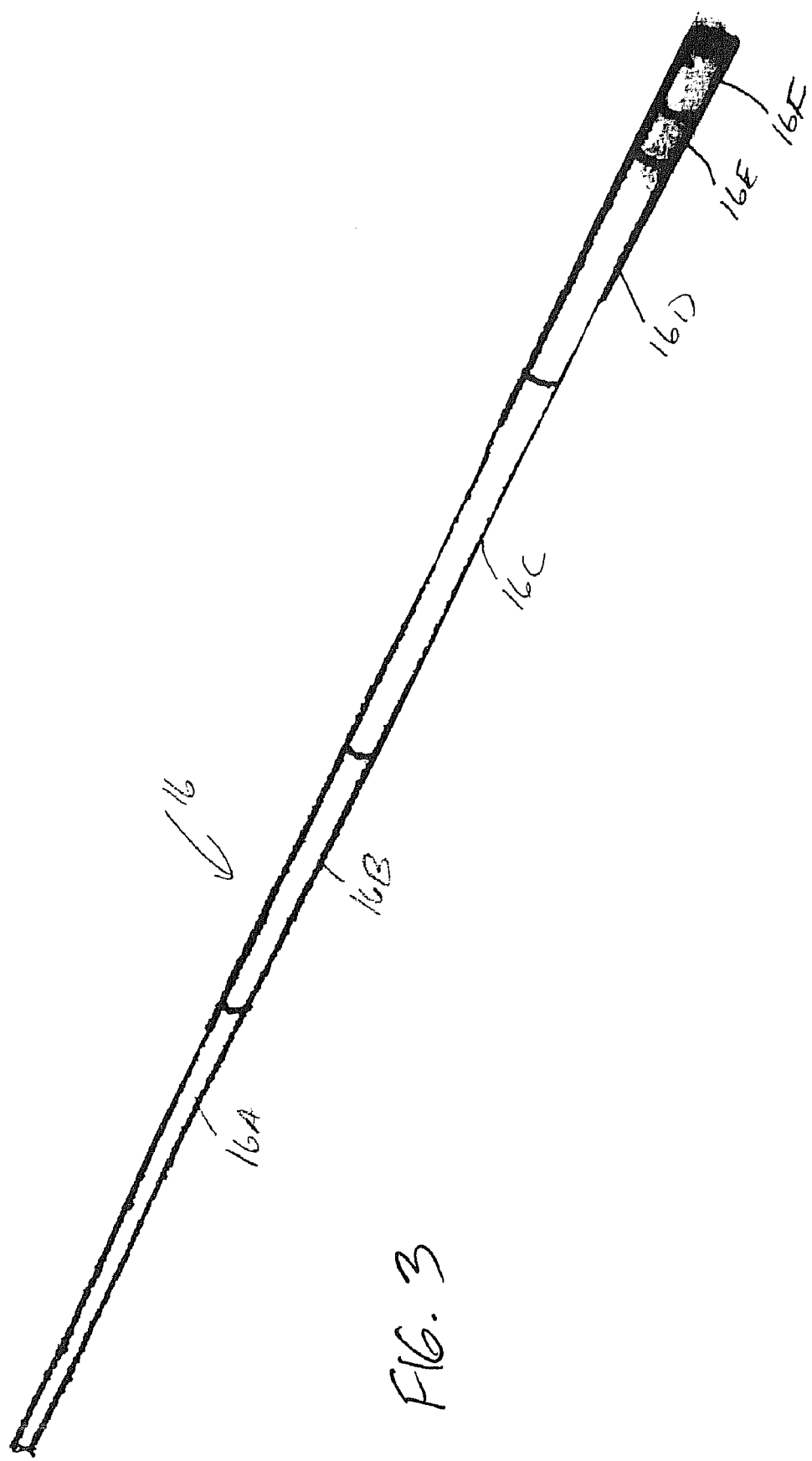
FIG. 3 is a perspective view of a multi-segmented guide catheter shaft in accordance with the present invention.
Figure 4:
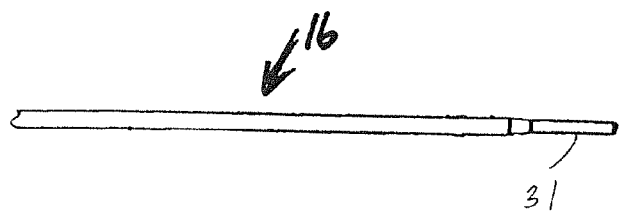
FIG. 4 is a plan view of a reduced diameter distal tip suitable for use as part of the guide catheter of FIG. 1.

A fitting (or hub) 18 and possibly a handle 19 may be coupled to the proximal end 12 as shown. The elongate shaft 16 may be formed from a unitary segment, or from multiple segments (for example the segments 16A, 16B, 16C, 16D, 16E, 16F as shown in FIG. 3) that are joined together as is well known. Such multiple segments may have varying flexion characteristics if desired. The elongate shaft 16 may be formed to provide a straight shape or bent shape depending on the desired application. The elongate shaft 16 may have a reduced diameter distal tip 31 at the distal end as shown in FIG. 4 and described in U.S. Patent App. No. 2004/0073158, incorporated by reference herein in its entirety. The reduced diameter distal tip 31 facilitates cannulation of a vessel.

Figure 2:
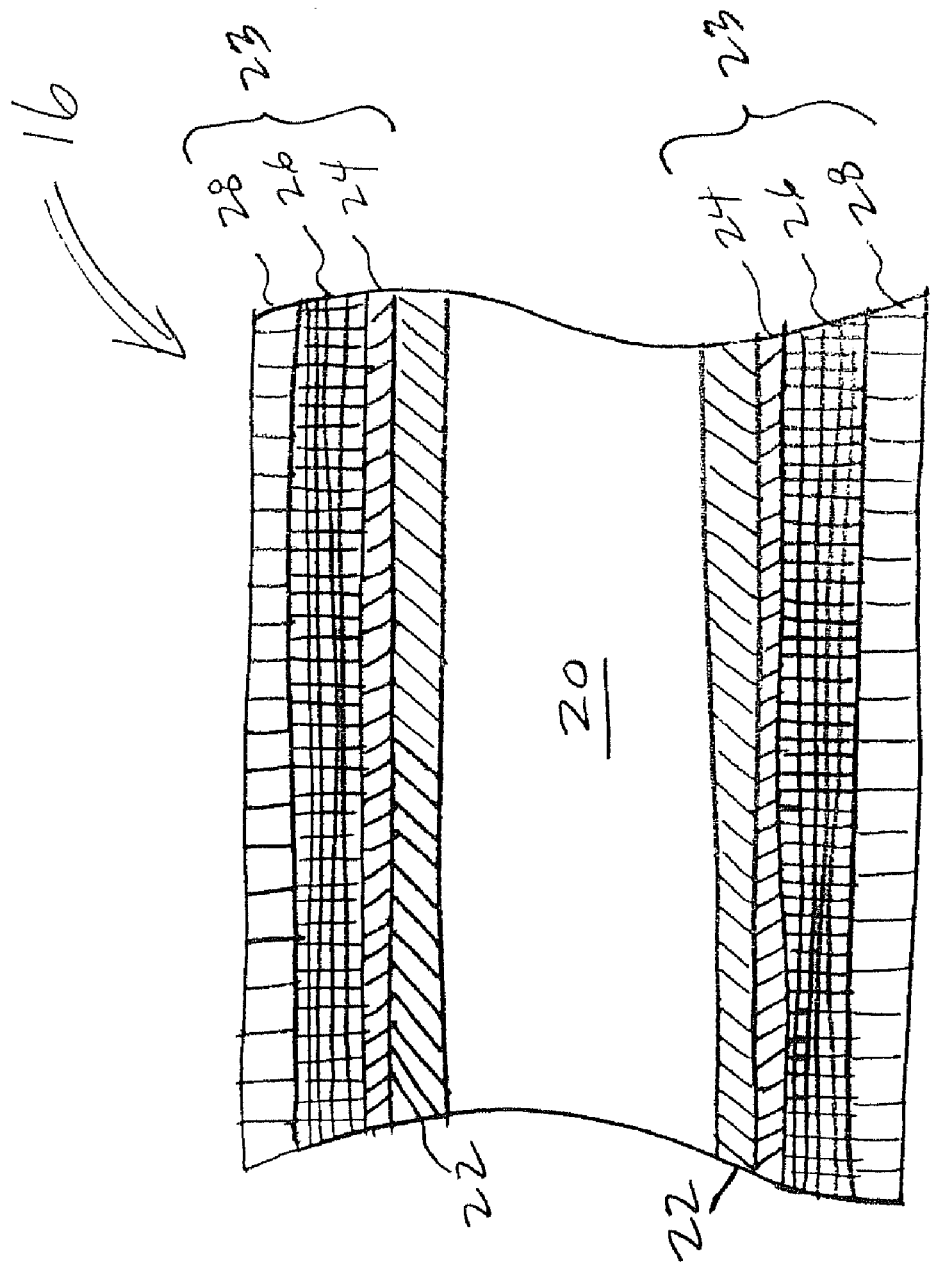
FIG. 2 is a cross-sectional view of the hollow elongate shaft of the guide catheter of FIG. 1 in accordance with the present invention.

FIG. 2 is a cross-sectional side view of the hollow elongate shaft 16 of FIG. 1 (or hollow elongate shaft segment of FIG. 3) in accordance with the present invention. The channel 20 is defined by the lumen of an inner tube 22, which is formed from a synthetic polymeric material. Preferably, the synthetic polymeric material is lubricious, such as PTFE, polyethylene, or the like, to facilitate passage of devices and/or agents through the channel 20 formed by the inner tube 22. A multilayer sheath 23 is formed about the outer surface of the inner tube 22. The multilayer sheath 23 includes reinforcing material 24, an intermediate layer 26 formed from a melt-processible polyether-block amide material (e.g., PEBAX®) and an outer layer 28 formed from a different polyether-block amide material. Preferably, the polyether-block amide layer of the outer layer 28 provides a shrink tube with a shrink temperature range greater than the melt temperature range of the polyether-block amide material of the intermediate layer 26. In this configuration, the elongate shaft is formed by heating the intermediate layer 26 and outer layer 28 within the shrink temperature range such that the outer layer shrinks and the intermediate layer melts to thereby bond the multilayer sheath to the inner tube as described below. The outer layer 28 preferably has a hardness that is substantially similar to the hardness of the intermediate layer 26. In addition, the melt-processible polyether-block amide material of the outer layer 28 is preferably cross-linked and may be formed by processing the same (or similar) polyether-block amide material of the intermediate layer 26 with ultra-violet radiation or other suitable techniques.

The reinforcing material 24 may be formed by braiding reinforcing filaments about the outer surface of the inner tube 22 as is well known. In this configuration, the reinforcing material is typically not a continuous layer about the outer surface of the inner tube as shown, but is wound about the outer surface in a mesh pattern leaving openings to the outer surface of the inner tube. Such reinforcing filaments may be a variety of metallic materials (such as steel), or plastic materials (such as polyester). In addition, radio-opaque material (such as platinum, iridium, gold, tantalum, tungsten carbide and the like) may be used to form the filaments to facilitate fluoroscopic imaging techniques. Echogenic material (such as a composite material of jet milled tungsten carbide and polymeric material as described in U.S. Patent App. No. 2004/0073158) may also be used to form the filaments to facilitate guiding of the catheter utilizing ultrasonic imaging techniques. In addition, material that is both radio-opaque and echogenic (e.g., a polymer, such as PEBAX®, together with an appropriate radio-opaque and echogenic filler, such as tungsten carbide particles), may be used to form the filaments of the reinforcing braid.

Similarly, the polyether-block amide layer 26 and/or the polyether-block amide layer 28 may have a radio-opaque filler material (such as platinum, iridium, gold, tantalum, tungsten carbide and the like), an echogenic filler material (such as a composite material of jet milled tungsten carbide and polymeric material as described in U.S. Patent App. No. 2004/0073158), or a material that is both radio-opaque and echogenic to facilitate guiding of the catheter utilizing fluoroscopic imaging techniques and/or ultrasonic imaging techniques.

Preferably, the elongate shaft 16 of the guide catheter 10 is formed as follows. First, the inner tube 22 is formed by coating a mandrel with a synthetic polymeric material and then extruding the coated mandrel through a die. As set forth above, the synthetic polymeric material is preferably lubricous, such as a PTFE, polyethylene or the like, to facilitate passage of devices through the channel 20 formed by the inner tube 22. Preferably, the mandrel has a diameter of at least 3 French such that the lumen of the inner tube 22 (which is formed when the mandrel is removed) has a corresponding size. Such sizes are suitable to allow introduction of a broad array of medical devices used in modern intravascular and coronary applications. For example, an inner tube that provides a 3 French lumen provides the necessary clearance for guiding a catheter device having a 1 French outer diameter. Note however that the size of the lumen of the inner tube 22 may be readily changed (increased or decreased) for the desired application(s).

Reinforcing material 24 is then formed about the outer surface of the inner tube 22. Preferably, the reinforcing material 24 is formed by braiding reinforcing filaments about the outer surface. In this configuration, the filaments are wound about the outer surface in a mesh pattern leaving openings to the outer surface of the inner tube 22. The filaments may be a variety of metallic materials (such as steel), or plastic materials (such as polyester). In addition, radio-opaque material (such as platinum, iridium, gold, tantalum, tungsten carbide and the like) may be used to form the filaments to facilitate fluoroscopic imaging techniques. Echo-visible material (such as a composite material of jet milled tungsten carbide and polymeric material as described in U.S. Patent App. No. 2004/0073158) may also be used to form the filaments to facilitate ultrasonic imaging techniques. In addition, material that is both radio-opaque and echogenic (e.g., a polymer, such as PEBAX®, together with an appropriate radio-opaque and echogenic filler, such as tungsten carbide particles), may be used to form the filaments of the reinforcing braid.

The inner tube 22 with the reinforcing material 24 applied thereto is coated with a polyether-block amide material and then extruded through a die to form a sheath 26. Examples of suitable polyether-block amide materials are marketed under the trademark PEBAX® and commercially available from Atofina Chemicals Inc. of King of Prussia, Pa. More particularly, PEBAX® is a trade name for a family of melt-processible polyether-block amide materials that have good hydrolytic stability and are available in a broad range of stiffnesses. In addition, PEBAX® accepts various colors and fillers (including radio-opaque and/or echogenic fillers. PEBAX® has a melt temperature range between 335° F. and 400° F.

Shrink tubing 28 formed from a different polyether-block amide material is placed over the assembly (e.g., covering the intermediate sheath 26). The polyether-block amide material of the shrink tubing 28 has a shrink temperature range above the melt temperature range for the intermediate sheath material. An example of suitable material for use in the shrink tubing 28 is a cross-linked polyether-block amide material, which is found in the shrink tubing marketed under the trademark PALLADIUM PEBAX® HEAT SHRINK TUBING and commercially available from Cobalt Polymers of Colverdale, Calif. This shrink tubing has a shrink temperature range between 340° F. and 600° F. At the higher end of this temperature range, the heat must be applied for a short period of time to avoid degradation of the shrink tubing.

The resulting assembly is heated at a temperature within the shrink temperature range of the tubing 28 (for example, at a temperature of 340° F. for the PALLADIUM PEBAX® HEAT SHRINK TUBING. This activates the shrink tube layer 28 (i.e., it shrinks) and the material of the intermediate sheath 26 melts. As the shrink tube layer 28 shrinks, it forces the molten material of the intermediate sheath 26 around the reinforcing material 24 and through the openings formed by the braid structure to contact the inner tube 22, thereby bonding the multilayer sheath structure to the inner tube structure. Note that the shrink tubing layer 28 remains as part of the final shaft assembly.

The mandrel is then removed from the assembly to form the elongate shaft 16. This is preferably accomplished by pulling on the mandrel whereby the lubricious nature of the inner tube 22 allows the inner tube 22 to be easily separated from the elongate shaft structure.

Figure 5:
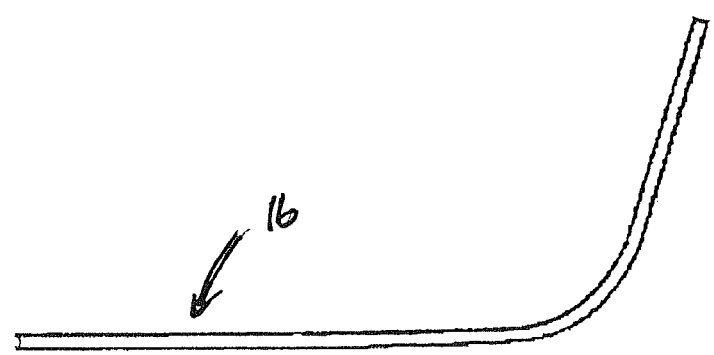
FIG. 5 is a plan view of a guide catheter shaft with a curved contour at its distal end in accordance with the present invention.
Figure 6:
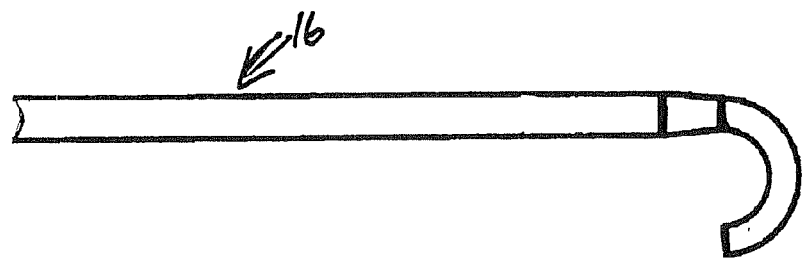
FIG. 6 is a plan view of a guide catheter shaft with a hooked contour at its distal end in accordance with the present invention.
Figure 7:
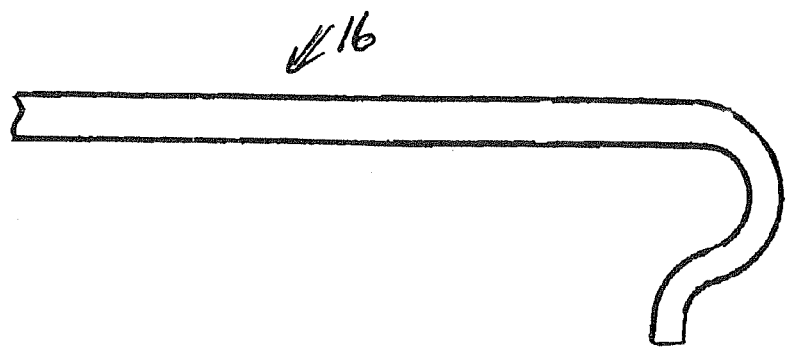
FIG. 7 is a plan view of a guide catheter shaft with a compound-curved contour at its distal end in accordance with the present invention.

The profile and length of the elongate shaft of the guide catheter described herein may be optimized for the intended method of access. For example, the contour of the hollow elongate shaft may be bent to form a curve, hook or compound curve as shown in FIGS. 5, 6, and 7, respectively. Preferably, such contours are achieved by constraining the elongate shaft in a shaping fixture while heating the shaft 16 until it assumes the intended contour (e.g., by "heat setting" the shaft 16).

The guide catheter shaft structure as described above may be used to form a unitary guide lumen as shown in FIG. 1, or may be used to form a guide lumen segment that is coupled to the other guide lumen segments as shown in FIG. 3. The multiple guide lumen segments may have varying flexion characteristics, different material characteristics (such as different fillers for controlling the radio-opaqueness and/or echogenicity of the segments), and different shapes. Moreover, the reinforcing braid of the guide catheter shaft structure as described above may be omitted to provide for greater flexibility.

Advantageously, the guide catheter shaft (or shaft segment) of the present invention has lower material costs because the PEBAX®-based shrink tubing has a lower cost than the fluorinated ethylene-propylene (FEP) shrink tubing typically used in the prior art devices. The manufacturing process is also simplified because the process and tooling that removes the FEP shrink tubing (or other type shrink tubing) can be avoided. Finally, where PEBAX® is used in commercially-available products, it is likely that regulatory resubmission of the device can be avoided.

There has been described and illustrated herein an embodiment of an improved guide catheter (and improved guide catheter shaft) that employs a flexible intermediate sheath formed from a melt-processible first polyether-block amide material along with an outer sheath formed from a different second polyether-block amide material. The first polyether-block amide material has a melt temperature in the shrink temperature range of the second polyether-block amide material. While particular embodiments of the invention have been described, it is not intended that the invention be limited thereto, as it is intended that the invention be as broad in scope as the art will allow and that the specification be read likewise. Thus, while particular geometries and dimensions of the assembly elements have been disclosed, it will be understood that other geometries and dimensions can be used. Moreover, while particular configurations and materials have been disclosed, it will be appreciated that other configurations and materials could be used as well. It will therefore be appreciated by those skilled in the art that yet other modifications could be made to the provided invention without deviating from its spirit and scope as claimed.

What is claimed is:

1. A method of forming a guide catheter shaft, comprising:
   forming an inner tube structure;
   forming a multilayer sheath around the inner tube structure, the multilayer sheath including an intermediate sheath and a shrink tube layer, said intermediate sheath around the inner tube structure, the intermediate sheath comprising a melt-processible first polyether-block amide material, said shrink tube layer around the intermediate sheath, and said shrink tube layer comprising a second polyether-block amide material that has a shrink temperature range greater than a melt temperature range of said first polyether-block amide material; and
   heating the resulting structure at a temperature within the shrink temperature range of the shrink tube layer, thereby causing the second polyether-block amide material to shrink and the first polyether-block amide material to melt, and bonding the multilayer sheath to the inner tube structure.

2. A method according to claim 1, further comprising:
   applying reinforcing material around the inner tube structure such that it is disposed between the inner tube structure and the intermediate sheath.

3. A method according to claim 1, wherein:
   said second polyether-block amide material comprises a cross-linked polyether-block amide material.

4. A method according to claim 1, wherein:
   said inner tube structure is formed from a synthetic polymeric material.

5. A method according to claim 4, wherein:
   said inner tube structure is formed by coating a mandrel with a synthetic polymeric material and then extruding the coated mandrel through a die.

6. A method according to claim 4, wherein:
   said synthetic polymeric material is lubricous.

7. A method according to claim 5, wherein:
   said synthetic polymeric material comprises one of PTFE and polyethylene.

8. A method according to claim 2, wherein:
   said reinforcing material is applied around said inner tube structure by braiding reinforcing filaments about said inner tube structure.

9. A method according to claim 8, wherein:

said reinforcing filaments comprise one of a metallic material and plastic material.

10. A method according to claim 8, wherein:

said reinforcing filaments comprise a radio-opaque material.

11. A method according to claim 8, wherein:

said reinforcing filaments comprise an echogenic material.

12. A method according to claim 1, wherein:

a portion of said guide catheter shaft is formed to have one of a straight shape and a bent shape.

13. A method according to claim 12, wherein:

said bent shape comprises one of a curve, hook, and compound curve.

* * * * *